(12) United States Patent
Ivory et al.

(10) Patent No.: US 7,938,946 B2
(45) Date of Patent: May 10, 2011

(54) VORTEX-STABILIZED ELECTROPHORETIC DEVICES AND METHODS

(75) Inventors: Cornelius Ivory, Pullman, WA (US); Noah Tracy, Pullman, WA (US); Dan M. Leatzow, Butte, MT (US)

(73) Assignees: Protasis Corporation, Marlborough, MA (US); Washington State University Research Foundation, Pullman, WA (US)

( * ) Notice: Subject to any disclaimer, the term of this patent is extended or adjusted under 35 U.S.C. 154(b) by 1093 days.

(21) Appl. No.: 10/544,511

(22) PCT Filed: Feb. 6, 2004

(86) PCT No.: PCT/US2004/003490
§ 371 (c)(1),
(2), (4) Date: Mar. 6, 2006

(87) PCT Pub. No.: WO2004/072611
PCT Pub. Date: Aug. 26, 2004

(65) Prior Publication Data
US 2006/0219556 A1    Oct. 5, 2006

Related U.S. Application Data

(60) Provisional application No. 60/446,287, filed on Feb. 6, 2003.

(51) Int. Cl.
*C02F 1/38* (2006.01)
*G01N 27/00* (2006.01)

(52) U.S. Cl. ........................................ 204/600; 204/601

(58) Field of Classification Search .................. 204/450, 204/451, 600, 601
See application file for complete search history.

(56) References Cited

U.S. PATENT DOCUMENTS

| | | | |
|---|---|---|---|
| 4,040,940 A | 8/1977 | Bier | |
| 4,200,614 A | 4/1980 | Colburn et al. | |
| 4,588,492 A | 5/1986 | Bier | |
| 4,617,103 A | 10/1986 | Lovegrove | |
| 4,900,421 A | 2/1990 | Grutzner et al. | |
| 5,298,143 A | 3/1994 | Ivory et al. | |
| 5,360,195 A * | 11/1994 | Young | 248/550 |
| 6,277,258 B1 | 8/2001 | Ivory et al. | |
| 6,793,791 B2 | 9/2004 | Bier | |
| 2003/0006142 A1 | 1/2003 | Nair et al. | |
| 2003/0094369 A1 | 5/2003 | Tolley et al. | |

OTHER PUBLICATIONS

Wronski, S., et al. "Dynamic filtration in biotechnology", Bioprocess Engineering, vol. 4, no month given, 1989, p. 99-104.*

(Continued)

*Primary Examiner* — Ula C Ruddock
*Assistant Examiner* — J. Christopher Ball
(74) *Attorney, Agent, or Firm* — Banner & Witcoff, Ltd.

(57) ABSTRACT

A vortex-stabilized electrophoretic processor comprises an annular processing chamber at least partly defined by concentric first and second processing chamber surfaces. At least one of the processing chamber surfaces is rotatable relative to the other processing chamber surface. The electrophoretic processor further comprises an electric field generator operative to be energized to establish a dynamic field gradient within the processing chamber. At least one fluid port is provided, having fluid communication with the processing chamber. The electric field generator may comprise an elongate electrode array positioned within a central bore of a rotor forming the inside surface of the processing chamber. One or both of the processing chamber surfaces can have shaping comprising multiple spaced tines or annular ridges extending toward the other of the processing chamber surfaces.

44 Claims, 10 Drawing Sheets

OTHER PUBLICATIONS

B. M. Thome, Master's Thesis, Washington State University, Department of Chemical Engineering, Aug. 2001, chapter 2, p. 28-62.*

Article entitled, "Taylor-Couette Flow", page reference not available, found at URL:http://www.mech.nwu.edu/fac/lueptow/HTML/taylor-coutteflow.html.

S. Douglass Gilman, University of Tennessee and Mark A. Hayes, Arizona State University, "Electroosmosis in Microfluidic Devices: If Only We Could Control and Measure It!", Abstract (2 pp.) from symposium presented at PITTCON ® 2003, held at the Orange County Convention Center in Orlando, Florida, Mar. 9-14, 2003.

M.T. Blom[1], E.F. Hasselbrink[2], H. Wensink[1], A. Van Den Berg[1], "Solute Dispersion by Electroosmotic Flow in Nonuniform Microfluidic Channels", [1]University of Twente, MESA Research Institute, Enschede, The Netherlands; [2]Sandia National Laboratories, P.O. Box 969, MS 9951, Livermore, CA 94550.

B. Thome, C.F. Ivory, J. Chromatogr A. 953 (2002) 268.

Patrick H. O'Farrell, "Separation Techniques Based on the Opposition of Two Counteracting Forces to Produce a Dynamic Equilibrium", *Science* 1985, 227, 1586-1589.

Cornelius F. Ivory, "The Prospects for Large-Scale Electrophoresis", *Separation Science and Technology*, 23(8 &9), pp. 875-912, 1988.

Bruce R. Locke and Ruben G. Carbonell, "A Theoretical and Experimental Study of Counteracting Chromatographic Electrophoresis", *Separation and Purification Methods*, 18(1), 1-64 (1989).

Cornelius F. Ivory and William A. Gobie, "Continuous Counteracting Chromatographic Electrophoresis", *Biotechnol. Prog.* 1990, 6, 2-32.

Wendy S. Koegler and Cornelius F. Ivory, "focusing Proteins in an Electric Field Gradient", J. Chromatogr., A 229 (1996) 229-236.

Robert D. Greenlee and Cornelius F. Ivory, "Protein Focusing in a Conductivity Gradient", *Biotechnol. Prog.* 1998, 14, 300-309.

C.F. Ivory and N. Tracy, "Dynamic Electrofocusing at Milligram Scales", American Institute of Chemical Engineers (AIChE)/American Electrophoresis Society (AES) National Meeting in 2003, Washington State University, 54 page presentation.

Cornelius F. Ivory, "*Alternative Electrofocusing Methods*", Department of Chemical Engineering, Washington State University, Pullman, WA, pp. 298-318.

Cornelius F. Ivory, "Preparative Free-Flow Electrofucusing ina Vortex-Stabilized Annulus", *Eletrophoresis* 2004, 25, 360-374.

Noah I. Tracy and Cornelius F. Ivory, Poster entitled, Modeling Dynamic Field Gradient Focusing, Washington State University, Department of Chemical Engineering, Pullman, Washington.

Noah I. Tracy and Cornelius F. Ivory, Presentation entitled, "Scaling Up Dynamic Field Gradient Focusing", Nov. 18, 2003, Washington State University, Department of Chemical Engineering, Pullman, Washington.

Zheng Huang and Cornelius F. Ivory, "Digitally Controlled Electrophoretic Focusing", *Analytical Chemistry*, vol. 71, No. 8: 1628-1632, Apr. 15, 1999.

Kelly R.T. And Woolley A.T., "Electric Field Gradient Focusing", *Journal of Separation Science* 28 (15): 1985-1993 Oct. 2005.

* cited by examiner

VORTEX-STABILIZED ELECTROPHORETIC DEVICES AND METHODS

CROSS-REFERENCE TO RELATED APPLICATIONS

This application is a 35 U.S.C. §371 National Phase filing of PCT Application No. PCT/US04/003490 filed 6 Feb. 2004, which application claimed priority of the following commonly owned U.S. Provisional Patent Application Ser. No. 60/446,287, filed 6 Feb. 2003. The PCT application designated the United States and was published in the English language on 26 Aug. 2004 as WO 04/072611.

TECHNICAL FIELD

The technical field of this invention is electrophoretic processors and related methods of electrophoretic processing of analytes in solution, e.g., electrophoretic focusing of proteins.

BACKGROUND

Electrophoresis is a generally inexpensive method of focusing analyte molecules, e.g., proteins, based on their movement in an electric field. Electrophoresis can be carried out in free solution or with the aid of a support medium, such as a gel, polymer solution, or granular packing. Electrophoresis typically employs a buffered electrolyte to maintain pH and provide sufficient conductivity to allow the passage of current. Electrophoretic focusing techniques have been described by a well known flux equation, with focusing occurring at the point in the processing chamber where the net gradient vanishes. A method known as counteracting chromatographic electrophoresis (CACE) has been used to focus proteins at the interface between two different gel filtration media packed into the upper and lower halves of an electrochromatography column. *Science* 1985, 227, 1586-1588. At least one protein, ferritin, could be concentrated beyond 100 mg/mL. *Sep. Sci. Technol.* 1988, 23, 875; *Sep. Purif. Methods* 1989, 18,1. This sucees was tempered, however, by the finding that this approach worked poorly with protein mixtures and would be difficult to scale up. *Biotechnol. Prog.* 1990, 6, 21.

It has been demonstrated that charged proteins can be focused, e.g., separated, concentrated, etc., using an electric field gradient in an electrochromatography column. Koegler and Ivory, *J. Chromatogr.*, A 1996, 229, 229-236. A fluted cooling jacket was used to form a linear gradient in the electric field which drove the proteins against a constant flow of buffer in a packed dialysis tube. This approach was slow and cumbersome and gave mediocre results, but it successfully illustrated a focusing technique known as electric field gradient focusing (EFGF). It also has been shown that proteins would focus in the electric field gradient formed by an axial conductivity gradient and opposed by a constant flow of buffer. Greenlee and Ivory, *Biotechnol. Prog.* 1998, 14, 300-309. The device was surprisingly fast when run in free solution, reaching equilibrium in less than 10 min., and gave unexpectedly good results when filled with a 40-μm size exclusion (SEC) packing. Focusing can also be achieved by opposing a constant convective velocity with a gradient in the electrophoretic velocity of the protein. This gradient can be created by varying the net charge on the protein (as in isoelectric focusing), by varying the cross-sectional area through which the electric current travels, as with electric field gradient focusing, or by varying the buffer conductivity. Isoelectric focusing (IEF) is a gradient focusing method which varies the charge on a protein using a pH gradient. The convective velocity is usually set to zero while the net charge on the protein decreases as it approaches its isoelectric point (pI). The protein focuses at this point since its net charge, and therefore its electrophoretic velocity, both vanish at its pI.

Conventional IEF is usually performed in a support medium such as agarose or polyacrylamide gel. The pH gradient is formed by using a complex set of reagents known as carrier ampholytcs which generate a stable, linear pII gradient under the influence of an applied electric field. Proteins migrate to the region where the ampholyte solution pH is equal to its own pI. In gels, detection of the focused bands involves a time consuming stain/destain procedure, and the ampholytes should be removed before the stain is applied. Established IEF protocols and a succinct history of its development are given by Righetti (1983).

Certain known electrophoretic systems utilize a confined chamber formed between two plates. An electric field is established between two opposing electrodes or in a desired two-dimensional array using additional electrodes. Such systems typically have good resolution of analytes, e.g., proteins, but have limited flow rates. Thus, electrophoresis has, in general, not been performed at flow rates adequately adapted to preparative scale production to provide significant quantities of a desired product. Filtration and chromatography, the principal methods used for preparative scale purification of biopharmaceuticals, have shortcomings, such as difficulty separating isoforms.

An electrophoretic method and apparatus for focusing solutes is described in U.S. Pat. No. 6,277,258 to Ivory et al., which is commonly assigned with the invention disclosed here and is hereby incorporated by reference in its entirety for all purposes. The disclosed apparatus utilizes a dynamic field gradient focusing (DFGF) method wherein dynamic electric field gradients are created, for example by a computer-controlled external circuit which manipulates the field strength generated by an array of electrodes. Dynamic field gradient focusing is well adapted to concentrate a target analyte or species from a dilute fluid sample, in certain cases being able to separate one or more such analytes from other species present in the fluid sample by concentrating them at different locations in the DFGF chamber. Such electrophoretic focusing takes advantage of the target analyte's charge to mass ratio or electrophoretic mobility as the fluid carrying the analyte is passed through an electric field gradient in a DFGF chamber. An electrophoretic approach such as DFGF can exploit small differences in net charge on an analyte molecule to separate isoforms by their electrophoretic mobilities. DFGF can be used to focus certain charged analytes, for example a desired protein, either on a batch-by-batch basis or in a continuous fashion. In addition, DFGF can be used in some cases to separate a desired analyte from other analytes in the same fluid sample, by concentrating the desired analyte at a location in the DFGF chamber at which the other analytes do not concentrate under the conditions used. The operative conditions typically include the sample flow rate, field strength and gradient, properties of the carrier fluid such as pH, chamber and electrode configuration, etc.

Electrophoretic devices and methods also are disclosed in U.S. Pat. No. 5,298,143 to Ivory et al., which is commonly assigned with the invention disclosed here and is incorporated herein by reference in its entirety for all purposes. Separation is performed, optionally with an electrode array, in an annular chamber formed between a fixed surface and a rotating surface. A disadvantage of the DFGF methods and devices disclosed by the Ivory et al. patents and others is that relatively small quantities of the desired concentrated product might be produced over a given period. Thus, for example, dynamic field gradient focusing was demonstrated to separate proteins by their electrophoretic mobility at the analytical scale in a device limited to microgram loads of protein (2.5 PE/PC, 10 Myo) using a small packed column to separate a cocktail of three proteins: phycoerythrin, phycocyanin, and myoglobin into two visible bands. Huang and Ivory, Anal. Chem. 1999.

Improvements are needed to increase the usefulness of electrophoretic processing of analytes. Notably, for example, improvements of known electrophoretic techniques are needed to scale-up DFGF for larger analyte loads. Scaling requires overcoming challenges in the areas of natural convection of the analyte in the processing chamber, cooling, and electrode arrangement. Natural convection will counteract focusing forces. Cooling, primarily dissipation of Joule heat, is important for certain analytes, such as proteins, since elevated temperatures can denature proteins.

Thus, despite advances in the electrophoretic methods and devices noted above, a need exists for electrophoretic methods and devices that can effectively focus analytes, e.g., separate charged solutes, such as protein mixtures, into their component solutes. The present invention seeks to fulfill these needs and provides further related advantages. Thus, it is an object of the present invention to address one or more of the above-mentioned research and industrial needs. It is an object of certain, but not necessarily all, exemplary embodiments of the invention to provide devices and methods for processing analytes, especially for focusing charged analytes, i.e., for concentrating and/or separating such charged analytes, e.g., separating charged analytes from other species in a fluid sample. From the following summary and the detailed description of certain exemplary embodiments, additional objects of the invention and objects of certain exemplary embodiments of the invention will be apparent to those skilled in the art, i.e., to those having skill and experience in this area of technology.

SUMMARY

In accordance with a first aspect, novel electrophoresis devices are provided which are operative under appropriate operating parameters and conditions to achieve effective analyte focusing. Certain preferred embodiments of these novel devices are operative to achieve effective analyte focusing at preparative scale. Such devices are operative to perform vortex-stabilized electrophoretic processing of analytes in a carrier fluid. DFGF is achieved in a vortex-stabilized electrophoretic processor. More specifically, a vortex-stabilized electrophoretic processor in accordance with this first aspect comprises an annular processing chamber at least partly defined by (i.e., is between) concentric, cylindrical processing chamber surfaces. At least one of the processing chamber surfaces is rotatable relative to the other processing chamber surface. In certain preferred embodiments one of the processing chamber surfaces is the surface of a rotor, i.e., a rotatable member mounted to or otherwise connected to a drive motor or the like, and the other surface of the processing chamber is the surface of a stator, a stationary member. The processor further comprises an electric field generator operative to be energized to establish a dynamic field gradient within the processing chamber. As discussed further below, in certain preferred embodiments the field generator comprises an electrode array. Electrodes of the electrode array are spaced axially along the processing chamber and each is independently controllable as to voltage level. At least one fluid port is provided in fluid communication with the processing chamber for the introduction of fluid into the processing chamber or for withdrawal of fluid from the processing chamber. More typically, an inlet port and an outlet port, each in fluid communication with the processing chamber, are provided at opposite ends of the processing chamber, with one or more take-off ports at spaced locations between the inlet and outlet ports, for removal or introduction of focused analyte, reactants, etc. At least one of the processing chamber surfaces has shaping comprising multiple spaced annular ridges extending toward the other processing chamber surface. During operation of the electrophoretic processor, with rotation of one or both of the processing chamber surfaces at adequate rotational speed (RPM), such shaping on one or both of the cylindrical surfaces of the processing chamber is effective to induce or to cooperate in establishing vortex-stabilized flow of the analyte-bearing fluid in the processing chamber. More specifically, the shaping, during rotation of the processing chamber surface(s) induces stable pairs of flow cells in the fluid sample in the processing chamber. Without wishing to be bound by theory, it currently is understood that the vortex cells circulate in a manner similar to Taylor cells or Couette flow.

During operation of certain preferred embodiments of the electrophoretic processors disclosed here, again without wishing to be bound by theory, it presently is understood that the aforesaid vortex-stabilized flow provides improved heat transfer, such that stronger electric field can be employed for faster focusing or other enhanced processing of analytes. The vortex-stabilized flow in the processing chamber also is presently understood to aid in the control of electroosmosis. Accordingly, such embodiments of the electrophoretic processor are found to be scalable to sizes suitable under typical operating parameters to process up to 25 mg loads or more of proteins or other analytes, focused at concentrations in up to 50 mg/mL or more.

In accordance with a method aspect of the present disclosure, vortex-stabilized electrophoretic processing comprises introducing a fluid sample comprising an analyte into an annular processing chamber of an electrophoretic processor as disclosed above. Vortex-stabilized flow of the fluid sample in the processing chamber is established by rotation of processing chamber surface(s). A dynamic field gradient is established in the processing chamber concurrent with the dynamic field gradient by energizing the electric field generator.

BRIEF DESCRIPTION OF THE DRAWINGS

The foregoing aspects and many of the attendant advantages of this invention will become more readily appreciated as the same become better understood by reference to the following detailed description, when taken in conjunction with the accompanying drawings, wherein.

It should be understood that the figures are not necessarily to scale, and that modification is possible to the relative size in dimensions of the various components. The same reference numbers are used to designate the same components in different figures.

DETAILED DESCRIPTION OF CERTAIN EXEMPLARY EMBODIMENTS

The present invention provides an electrophoretic device and method in which an analyte, typically a charged solute in a fluid sample, for example a protein, can be processed, such as by focusing and/or reaction with another specie in the fluid sample or with a reactant separately introduced into the processing chamber. For purposes of illustration the following discussion of the devices and methods disclosed here will primarily consider certain preferred embodiments wherein proteins present in dilute fluid samples are focused, more specifically, proteins are simultaneously separated and concentrated. It will be recognized by those of ordinary skill in the art that the principles employed in such certain preferred embodiments are applicable also to alternative embodiments of the invention. Similarly, for purposes of illustration the following discussion will primarily consider certain preferred embodiments wherein the analyte is processed in an annular chamber formed at least partly by an inner wall that rotates with respect to the outer wall, and wherein a constant first force, e.g. hydrodynamic force due to buffer flow, is opposed by a gradient in a second force, e.g., an electric field gradient established and maintained using an array of electrodes whose voltages are preferably individually monitored and dynamically adjusted by a computer-controlled circuit. The computer-generated electric field gradient allows charged molecules to be focused without using a pH gradient. For proteins, because the proteins are not focused at their pIs, precipitates do not form, so focused concentrations up to and even in excess of 50 mg/mL are possible in certain such embodiments. In addition, because the field shape is dynamically controlled from the computer on an electrode-by-electrode or other point-by-point basis, the field profile can be adjusted before and/or during a run to improve the resolution of components. Those skilled in this area of technology will recognize that additional and different features can be added to the embodiments discussed here without departing from the true scope and spirit of the invention.

Figure 1:
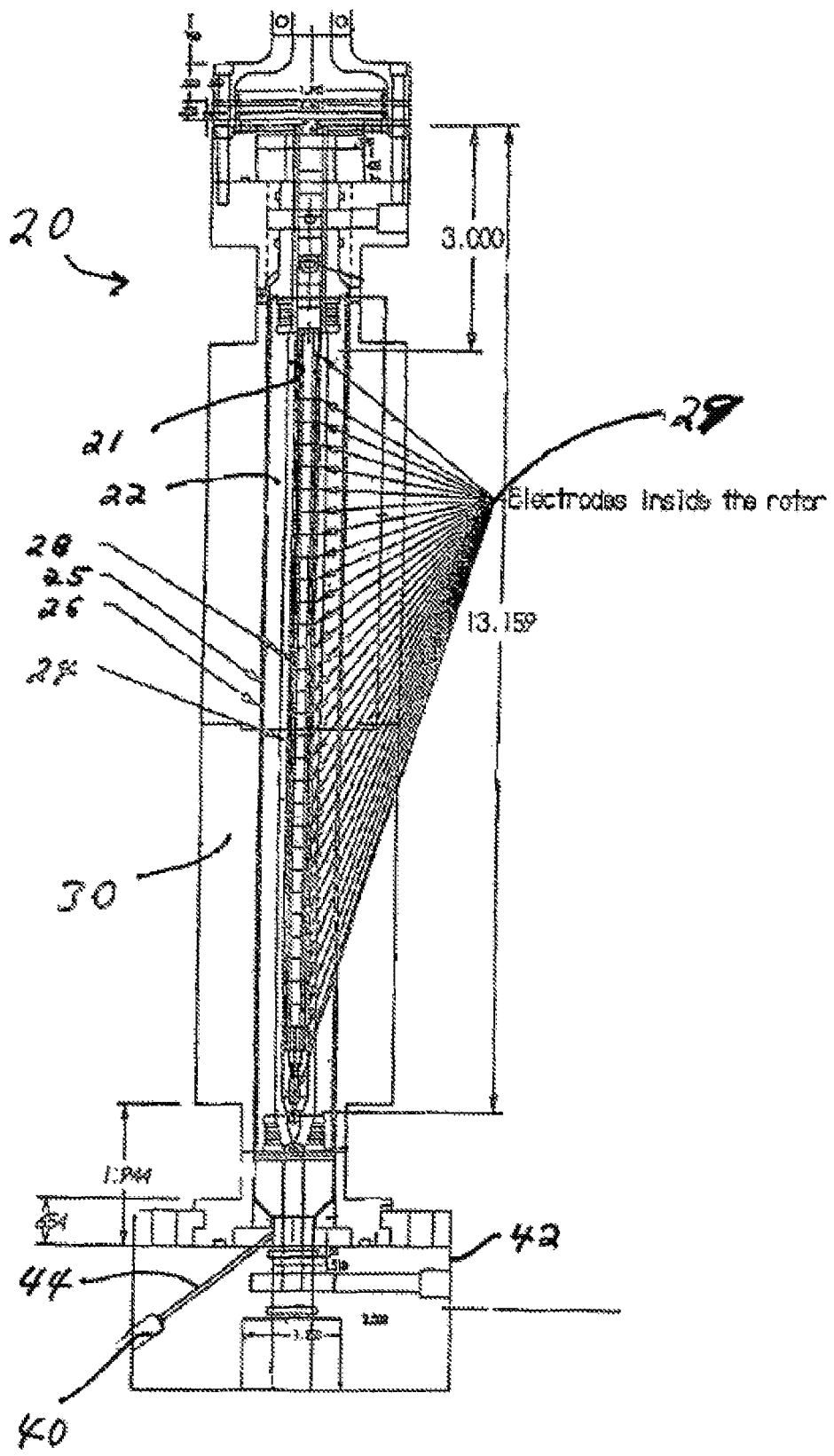
FIG. 1 shows a cross-sectional side elevation view of an electrophoresis device according to the present invention, including a vertically-oriented separation chamber containing a plurality of individually controlled electrodes.
Figure 2:
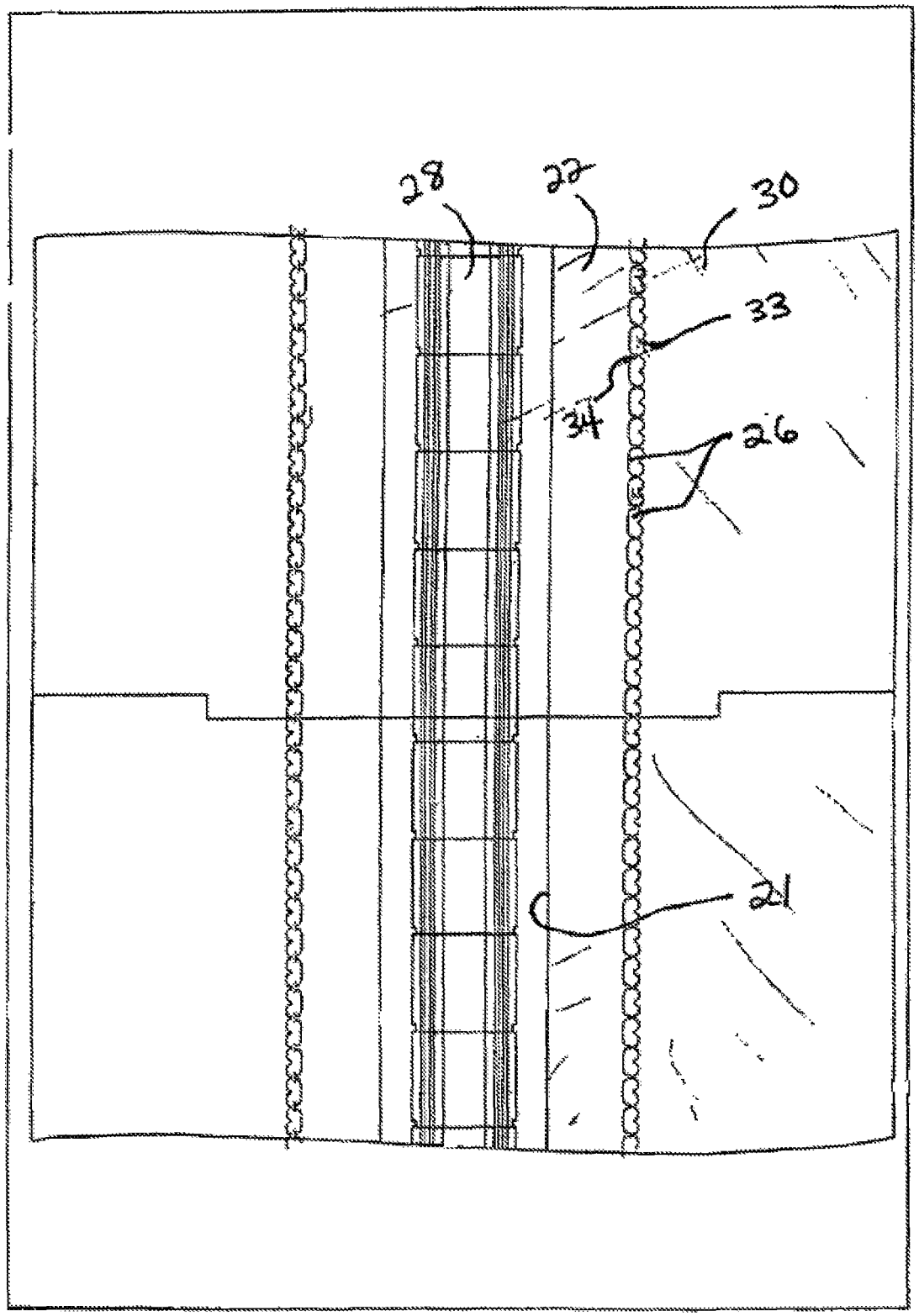
FIG. 2 shows a fragmentary enlarged side view of a portion of the device of FIG. 1, including a portion of the shaped annular separation chamber.

In the embodiment shown in FIGS. 1, 2 and 4-11, a separation tower 20 is vertically oriented. While alternative orientations can be used, better performance may be achieved vertically in view of the close tolerances between the inside and outside walls of the processing chamber and the rapid rotation of the rotor within the stator. The cylindrical rotor 22 is seen to have an inside wall 21 forming an axially extending central channel 24 concentric with the outer wall 25 of the rotor that forms the inside wall of the processing chamber 26. Such elongate central channel 24 serves as an electrode chamber housing an array of electrodes 28 operative when energized under operator control through a computer interface to establish a dynamic field gradient in the processing chamber. A motor rotates the rotor at a desired, controllable angular rate. A fluid, such as a native buffer, flows through the electrode chamber, cooling the electrodes. The buffer can be recirculated and/or cooled outside the electrode chamber. Optionally, auxiliary cooling means, e.g., a cooling jacket, etc. can be employed. The rotor may have any construction suitable to its functions. It should be sufficiently robust to maintain its form under the stresses of rotation and sufficiently porous to allow water or buffer ions to pass through. Suitable constructions include, for example, rigid tubes of porous materials such as ceramics, e.g., boron nitride. The rotor may include a membrane outer coating, i.e., an outer layer (in contact with fluid sample in the processing chamber) of a material that is ion permeable, but that is substantially impermeable to the desired product, for example the proteins or other target analyte. There are a number of suitable membranes commercially available, for example membranes used for dialysis, electrodialysis or nano-filtration. Alternatively, there are polymers and/or gels available that may be used. Thus, the processing chamber is in liquid and electrical communication with the electrode chamber through the porous rotor. Generally, an eluant is introduced into and flows through the processing chamber containing the charged solute Separation tower 20 further comprises a stator 30 concentrically disposed about the rotor 22. The stator and rotor define cooperatively between them the elongate annular gap that serves as the electrophoretic processing chamber 26. The stator can be formed of any suitably formable material, e.g., Plexiglas, which is sufficiently structurally robust for the intended use of the device. Other suitable materials for the stator and for each of the other components of the devices disclosed here will be apparent to those skilled in the art given the benefit of this disclosure. FIG. 2 is an enlarged section view of a portion of the processing chamber 26, showing the shaping of the surfaces of the rotor and stator. As discussed further herein, such surface shaping is operative during rotation of the rotor in the course of processing a fluid sample, to induce or encourage the formation of, and to maintain, circumferential vortices similar to Taylor vortices in Couette flow. Without wishing to be bound by theory, it is presently understood that such vortices are generated by the Taylor instability, and are counter-rotating pairs of vortices stacked axially (i.e., vertically in the orientation of FIGS. 1 and 2) along some or all of the length of the processing chamber. Thus, in operation, the rotor rotates within the stator at speeds sufficient to generate Taylor-like vortices. Suitable rotational speeds will be readily determined given the benefit of this disclosure and the general principle known by those skilled in the art regarding Taylor vortices in Couette flow. The dimensions of the processing chamber, including its radial dimension and the size and configuration of the annular ridges will impact the range of suitable rotational speeds for a given embodiment of the devices and methods disclosed here. Typically, in the absence of the annular ridges or other such surface shaping employed in the devices and methods disclose here, vortices typically emerge from the base Couette flow when the Taylor number, $$Ta = \frac{a\Omega^2 d^3}{v^2}\left(\frac{2\eta}{1+\eta}\right), \quad (6)$$

exceeds a critical value of about 1695 (Coles 1965; Katoaka 1386). The vortices are laminar, counter-rotating flow cells with an aspect ratio, height to thickness, of about 1. The cells are space-filling with their centers in nearly shear-free, solid-body rotation while circulation near the solid boundaries, i.e., rotor and stator, has a relatively higher shear. Pairs of adjacent vortex cells rotate in opposite directions to satisfy continuity of flow. A problem encountered with Taylor cells is the narrow range of Taylor number Ta over which they exist for a given system. Well-ordered, laminar Taylor cells are required in order for dispersion to be low. These appear in the annulus when a well-defined critical value of the angular velocity is reached, for example, about 30 RPM in certain systems. As the angular velocity is further increased, the vortices become stronger until they reach a second critical value at which wavy, vortices appear (Jones 1981). In practice, the wavy vortex modes increase the effective dispersion coefficient in the annulus to a point where, in a typical system, the contents of the annulus may be mixed throughout the chamber in less than about 60 seconds. The transition to wavy flow may typically occur when the angular velocity is increased by about 4% beyond the first critical value. Thus, such systems exhibit a small RPM operating range, severely hampering performance in such smooth rotor systems.

Figure 3:
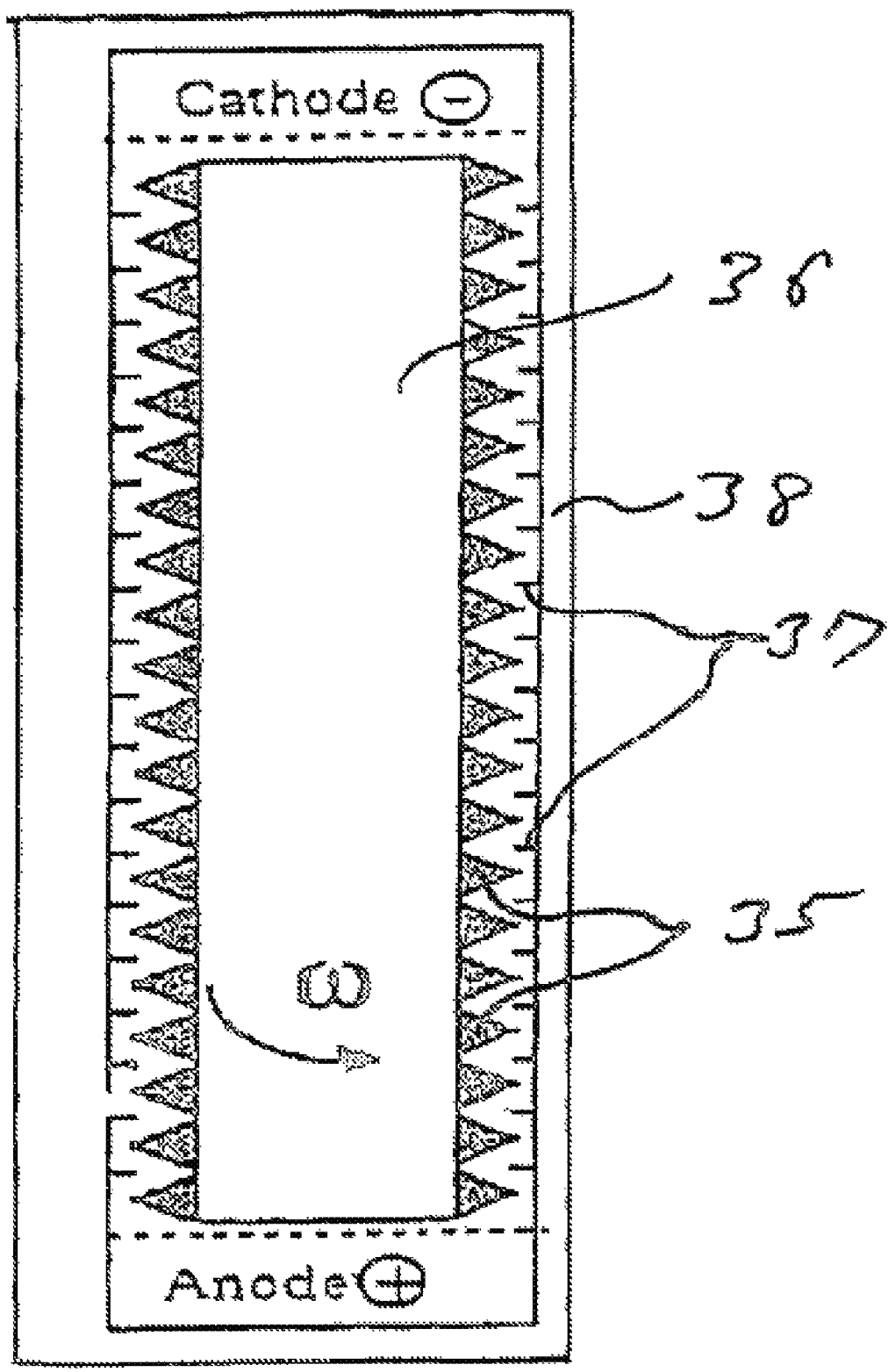
FIG. 3 shows a surface shape configuration for the surfaces of a rotor and a stator in accordance with alternative embodiment of the invention.

In the devices and methods disclosed here, shaping the rotor and/or stator induces stable flow cells. The shaping in the embodiment of FIG. 1, best seen in FIG. 2, is seen to be formed as axially narrow annular ridges 33 on the inside surface of the stator 30 and axially narrow annular ridges 34 on the outside surface of the rotor 22. The ridges on the rotor are spaced axially at twice the axial spacing of the stator ridges. As shown in the alternative embodiment of FIG. 3, such shaping may be configured as saw-tooth prominences 35 on a rotor 36 and ridges 37 on a stator 38. Rotation of the rotor with such surface shaping drags fluid around the annulus, directly imparting radial momentum to the fluid in contact with its surface. The imparted radial momentum is understood to be greatest at the zenith of the prominence, such that flow in the radial direction may originate at this point. Preferably the corrugations or other annular shaping features(s) are symmetric and their aspect ratio (radial dimension to axial dimension) is reasonable for the electrophoretic processor design overall, e.g., about 1:2 to 2:1, more preferably about 1.5:1 to 1:1.5, e.g., about 1 to 1, a typical flow of sample fluid in the processing chamber will break into pairs of cells and continuity will ensure that the vortex coils circulate in a manner similar to Taylor cells.

In certain preferred embodiments the surface shaping employed in the devices and methods disclose here also reduces electroosmosis and improves heat transfer. In smooth rotors and stators electroosmosis can drag solute across vortex boundaries and contribute disproportionately to dispersion. In exemplary embodiments of the present devices and methods, this effect can be significantly reduced by the surface shaping of the processing chamber. Without wishing to be bound by theory, it presently is understood that the surface shaping feature performs in the nature of a barrier, an electroosmosis "dam," in the absence of which solutes may more easily enter a poorly mixed stagnation zone on the rotor or stator where flow cells meet to begin their return to the opposite side of the annular gap. Such electroosmosis is a deleterious effect. It is believed that the dam, i.e., the shaping feature of such exemplary embodiments, interrupt the intercellular electroosmotic flow by forcing the electric field to change direction away from the rotor/stator base wall, effectively bending the electric field to discourage solutes from crossing flow cell boundaries and thereby reducing electroosmotic dispersion.

Shaping increases the effective heat transfer area in much the same way as fins, i.e., by extending the surface area for heat transfer (Welty, Wicks et al. 1984). Equilateral triangles placed on a flat surface with their vertices touching (see FIG. 3) have about twice the surface area as the flat surface on which they sit. Thus, the fins or other annular ridges can in certain preferred embodiments significantly increase the surface area and thereby significantly increase the heat transfer area. In addition, shaping can be used to eliminate or reduce regions of the flow cells, e.g., stagnation points, which would otherwise generate Joule heat without contributing significantly to heat transfer.

Certain preferred embodiments of the devices and methods disclosed here are operative to perform isoelectric focusing (IEF) in a vortex-stabilized chamber. In one such exemplary embodiment of IEF, a crude mixture of proteins, e.g., from cell homogenate or fermented beer, is first centrifuged or microfiltered to remove debris, then dialyzed against un appropriate buffer to reduce salt content, combined into a 0.25-2% ampholyte mixture and charged into the annulus, ie, into the elongate annular gap that serves as the processing chamber of the electrophoretic processor. The anode is continuously flushed with 1M phosphoric acid and isolated from the annulus using a cation exchange membrane. The cathode is flushed with 1M sodium hydroxide and isolated using an anion exchange membrane. After the current is tuned on, a pH gradient gradually forms along the axis of the annulus and is stabilized by the slight conductivity of the focused ampholytes (Righetti 1983). Commercial broad-range ampholyte mixtures normally yield nearly linear gradients running from about pH 3 at the anode to about pH 10 at the cathode. As the pH gradient establishes itself along the annulus, proteins migrate toward and then focus at their individual isoelectric points (Vesterberg 1971; Righetti 1983). Using broad-range ampholytes, such embodiments can resolve proteins with $\Delta pI=0.5$. Certain preferred embodiments of the devices and methods disclosed here, having a shaped rotor with a smooth stator, can provide a resolution of about 0.2 pH units using broad-range ampholytes. Generally, ampholyte concentrations as low as 0.2% work well with clean protein solutions in EE of the devices and methods disclosed here. However, with more complex solutions, higher concentrations of ampholytes may be beneficial or necessary and, if precipitates form it is usual to add solubilizing agents, e.g., 1-2% non-ionic or zwitterionic detergent first, then 6-8 M urea if needed. When precipitates form they focus into very tight bands and can be removed as isolated bands.

Significant advantage can be achieved using the devices and methods disclosed here. Use of certain embodiments designed as a preparative chamber, for example, will in certain instances circumvent the need for a parametric optimization study, e.g., performing run after run testing different combinations of ampholytes, modifiers and solvents to find conditions where isoforms are fractionated. Instead, the operator of the preparative chamber would be able to change field parameters during a run to optimize resolution and fractionate isoforms. Even the buffer itself can be changed during a run by replacing the inlet buffer and the coolant buffer with an alternative buffer system. Since the focusing chamber is segregated from the electrode chamber by a dialysis membrane, buffer exchange (including desalting) would be fast.

The device would not suffer the disadvantage of low solubility associated with focusing at the pI of a protein.

Given the benefit of this disclosure, numerous suitable alternatives will be apparent for the design of the electric field generator operative to be energized to establish the dynamic field gradient within the processing chamber. In certain preferred embodiments the electric field generator comprises an electrode array, for example, the electrode array positioned within the elongate cental opening of the rotor in embodiments shown in the Figures. The electrode design must not significantly disturb the vortex flows. One way to mount the electrode array on the annular chamber is to fix a vertical manifold on the stator. Such manifold array preferably extends from the base to the top of the annulus and houses each of the electrodes in a separate compartment that is purged by a common flow of buffer. In a typical embodiment, the rotor may be about 12 inches long, and corresponding manifold assemblies can accommodate about 25 electrodes mounted as matched, opposed pairs to avoid distortion of the electric field. A series of electrodes mounted on the side of the annulus in such fashion suffers electric field distortion low enough that the field is sufficiently smooth for electrofocusing.

Bands isolated or fractionated by a device or method disclosed here can be recovered from the processing chamber by sequentially draining the annulus through a series of off-take ports, preferably starting at the top of the chamber. It typically may require about 5 minutes to fill 20 to 25 off-take port syringes manually. Taking samples in this fashion helps minimize crosstalk, i.e., mixing between the off-take ports. Pulling a fraction from the center of the annulus without draining the upper ports typically results in significant crosstalk. However, in certain preferred embodiments of the devices and methods disclosed here, where the field gradient is set by the DFGF electrodes and not by ampholytes in the fluid, the gradient remains intact as samples are taken, even as makeup fluid is added to the chamber. Typically, the processing chamber can be used to elute samples during a run by first adjusting the field gradient to move the desired protein fraction(s) to an elution port. Once there, a portion of the current flowing through the annulus can be used to electrophoretically pull that fraction out of the chamber. While this is not possible with IEF since proteins are at their pIs and therefore have zero electrophoretic mobilities, DFGF focuses proteins away from their pI so electrophoretic elution is practical and only requires that a small amount of current be withdrawn from each off-take capillary. Alternatively, a fluid loop could be used to flush bands out of a port, e.g., using a separate peristaltic pump line for each off-take port.

Certain preferred embodiments further comprise global, online monitoring of proteins or other analytes during a run as they are separated in the chamber, preferably integrated with the computer that controls the field parameters. Given the benefit of this disclosure, those skilled in the art will recognize that there are several ways in which this can be done. A suitable approach is to install a set of fiber optic lines, perhaps 50 or more, on the stator. Each line would contain both source and detector and would feed back to a multiplexed diode-array detector, e.g., for UV-Vis or LIF detection or both. Using an array of detectors mounted on the chamber will allow real-time optimization of process speed and resolution as well as automated computer control of separation and recovery as described in the example below. With such global online monitoring implemented, certain preferred embodiments are further adapted for electronically-controlled focusing. Specifically, such embodiments comprise a control computer operative to automatically adjust the field parameters to optimize a separation. For example, a set of five recombinant protein isoforms with different electrophoretic mobilitiescan be focused near the inlet to the processing chamber designed for DFGF separation. The entire set could first be moved as a unit to the center of the chamber, e.g., by increasing the flow rate. Once the set is centered in the device, the isoform peaks can be spread over the length of the column by decreasing the electric field gradient so that the frontmost peak is near the inlet to the chamber and the rearmost peak is near the outlet. Both of these steps can be carried out by the computer, since with online monitoring the computer would know the position and breadth of the isoform bands as well as the local field strengths surrounding the bands. Next, the computer would scan the elongated isoform bands looking for isolated peaks and peaks with shoulders or other artifacts that suggest the presence of multiple isoforms. On finding one or more of these the computer then adjusts the electric field profile in the neighborhood of this band to tease out the overlapping peaks. If more room is needed for the shallow gradient, isolated peaks near the column outlet can be eluted and peaks closer to the inlet can be compressed at the top of the column. Thus, once the control computer can "see" the peaks, it can be programmed to automatically process them, improving and even in some cases essentially optimizing the separation of each component during the run.

In certain preferred embodiments the electrodes are mounted on a static cylinder inside the rotor. Wires, e.g., gold or platimun wires, run down through the interior of the cylinder and emerge at different points along its length. The wires are bent into symmetric ring electrodes or other suitable configuration for the particular device. Other electrode configurations may alternatively be used, including, e.g., an electrode cylinder mounted to rotate with the rotor. Also, e.g., it will be apparent to one of skill in the art, given the benefit of this disclosure, that the electrodes could alternatively be mounted in a chamber outside the stator. Placing the electrodes inside the rotor, however, eliminates the need for extra seals and membranes, as well as reducing or avoiding perturbation of the fraction collection system. Also, the engineered vortices that reduce natural convention in the processing chamber annulus would be unaffected or only affected to an acceptable degree by modifications made inside the rotor.

It will be appreciated that various embodiments of the methods and apparatus disclosed apparatus may be operated in a batch focusing mode, which requires a continuous cross-flow, or with suitable flow management means, e.g., a central feed port and two or more off-takes, may be operated continuously.

As disclosed above, the processing chamber is annular, meaning that the chamber defines a fluid-holding space that is ring-like, the ring-like space being more or less elongate, i.e., extending in a direction perpendicular to the circular cross-section, as desired for the intended use of the device. Typically, and in the embodiments shown in the appended Figures, the processing chamber is elongate with a ratio of chamber diameter to chamber length exceeding two to one, e.g., being from 5 to 1 up to 50 to 1 or greater. In this discussion and in the claims, the term axial and longitudinal are used interchangeably with reference to the processing chamber to mean the vertical direction or dimension of the chamber as it is oriented in the appended Figures. The processing chamber surfaces are rotatable relative each other. That is, one or both is mounted for rotation. Typically, and in the embodiments shown in the appended Figures, only one is operably connected to a rotational drive means, being referred to here and in the claims as the rotor. The other, not being rotatably driven, may be referred to as the stator. Either the inside or outside surface (or both) may be rotatably driven.

As disclosed above, one or both of the processing chamber surfaces has shaping, that is, has a non-smooth surface configuration, comprising multiple spaced annular teeth or, more generally, ridges. In the discussion below and in the claims, a processing chamber surface having shaping may be said to be "configured" or to be "shaped," all such terms having the same meaning here. The ridges are preferably symmetrical and have any size and aspect ratio (the ratio of radial dimension to longitudinal dimension) effective to facilitate the development of Couette flow or Taylor-like vortices during the intended use of the device with rotation of the processing chamber surface(s). As is generally understood by those skilled in the art, Taylor vortices are laminar, counter-rotating flow cells with an aspect ratio, height to thickness, of about 1. The cells are space-filling with their centers in nearly shear-free, solid-body rotation while circulation near the solid boundaries, i.e., rotor and stator, has a relatively higher shear. Pairs of adjacent vortex cells rotate in opposite directions to satisfy continuity of flow. The annular ridges may or may not each be a continuous, full circle. In some cases a ridge may be interrupted by a fluid port or other feature. The annular ridges typically lie, one each, in a series of parallel planes spaced from each other in a direction perpendicular to the planes, i.e., along the length of the chamber. Thus, in the elongate processing chamber of the exemplary embodiments seen in the appended Figures discussed further below, the ridges are spaced from one another along all or a portion of the longitudinal dimension of the chamber, and each ridge lies in a plane perpendicular to the longitudinal axis of the processing chamber. The ridges may have any suitable shape, typically but not necessarily being continuously uniform all the way around the circumference of the processing chamber surface. Exemplary cross-sectional shapes for a ridge include semi-circular, triangular and rectangular. In certain preferred embodiments the ridges of one surface are spaced from each other along the longitudinal direction of the processing chamber twice the distance between the ridges on the opposite surface. Thus, for example, where the device comprises a rotor inside a stator, as in embodiments shown in the appended drawings, the inside surface of the processing chamber is the outside of the rotor and the outside surface of the processing chamber is the inside surface of the stator. The ridges may in certain preferred embodiments form a saw-tooth pattern on either or both surfaces, with the distance between teeth or "period" of the shaping on the stator (measured along the axial direction of the processing chamber) being twice or one-half the distance between teeth on the rotor surface. The ridges may in certain preferred embodiments be narrow Preferably the apex of the teeth on one surface are precisely aligned (along the axial direction of the processing chamber) with those of the opposite surface.

As disclosed above, certain preferred embodiments of the electrophoretic processor comprises an electrode array or other electric field generator operative to be energized to establish a dynamic field gradient within the processing chamber. As used here and in the claims, a dynamic field gradient means an electric field for acting on a charged analyte in the processing chamber, which varies with location in the chamber and optionally also varies with time during processing of an analyte. Such variation is not merely a change in the strength or other aspect of its configuration that a field established between two electrodes might exhibit as a result of minor component imperfections or positioning or the like. Rather, a dynamic field gradient in the systems and methods disclosed here involves a field configuration that is controlled to vary along the length of the processing chamber, such that the rate of change of field strength, for example, increases or decreases (as a function of position in the processing chamber) faster or more slowly in one zone than in another. The field may even reverse direction of change in adjacent zones. More typically, the rate of change, i.e., the slope of the derivative, will be steeper in some zones than in others. In general, a steep slope will separate analytes faster, while a shallow slope may separate analytes to positions spatially more distant from each other in the processing chamber. In certain preferred embodiments employing an electrode array, a suitable number of electrodes is any number sufficient to establish the necessary or desired dynamic field gradient. While an array of as few as three independently controlled electrodes spaced longitudinally along an elongate processing chamber may be sufficient for certain intended applications, an electrode array in the devices and methods disclosed here will typically comprise a larger number, e.g., more than ten electrodes, preferably more than twenty electrodes, e.g., thirty to fifty electrodes. The electrodes preferably are independently, i.e., individually, controlled, typically by computer or other user interface to the power source, whereby the voltage at each can be set differently and changed individually. Optionally, the electrodes also can be controlled simultaneously or in sub-sets.

Figure 4:
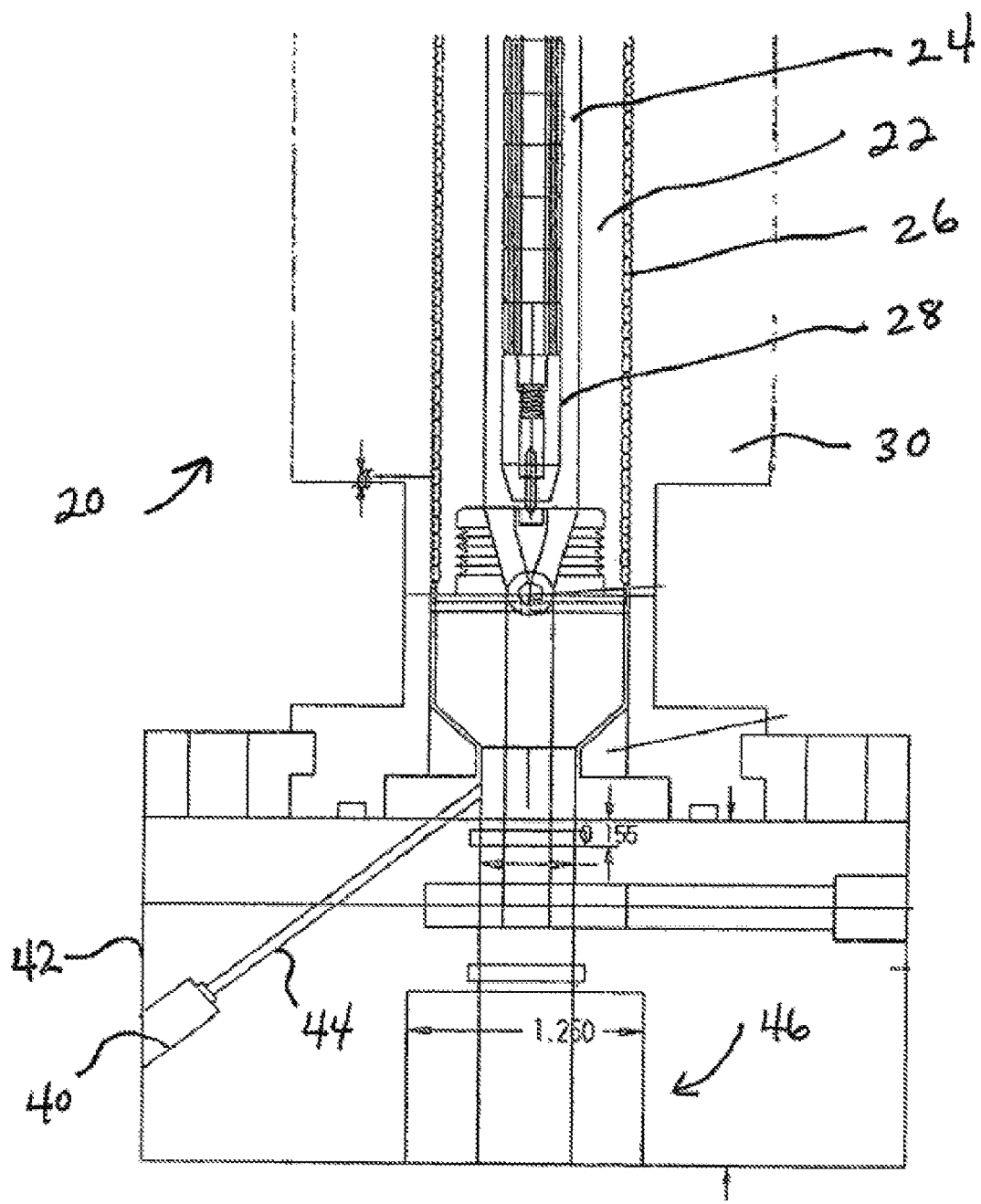
FIG. 4 is an enlarged section view, partially broken away, of the embodiment of FIG. 1.
Figure 5:
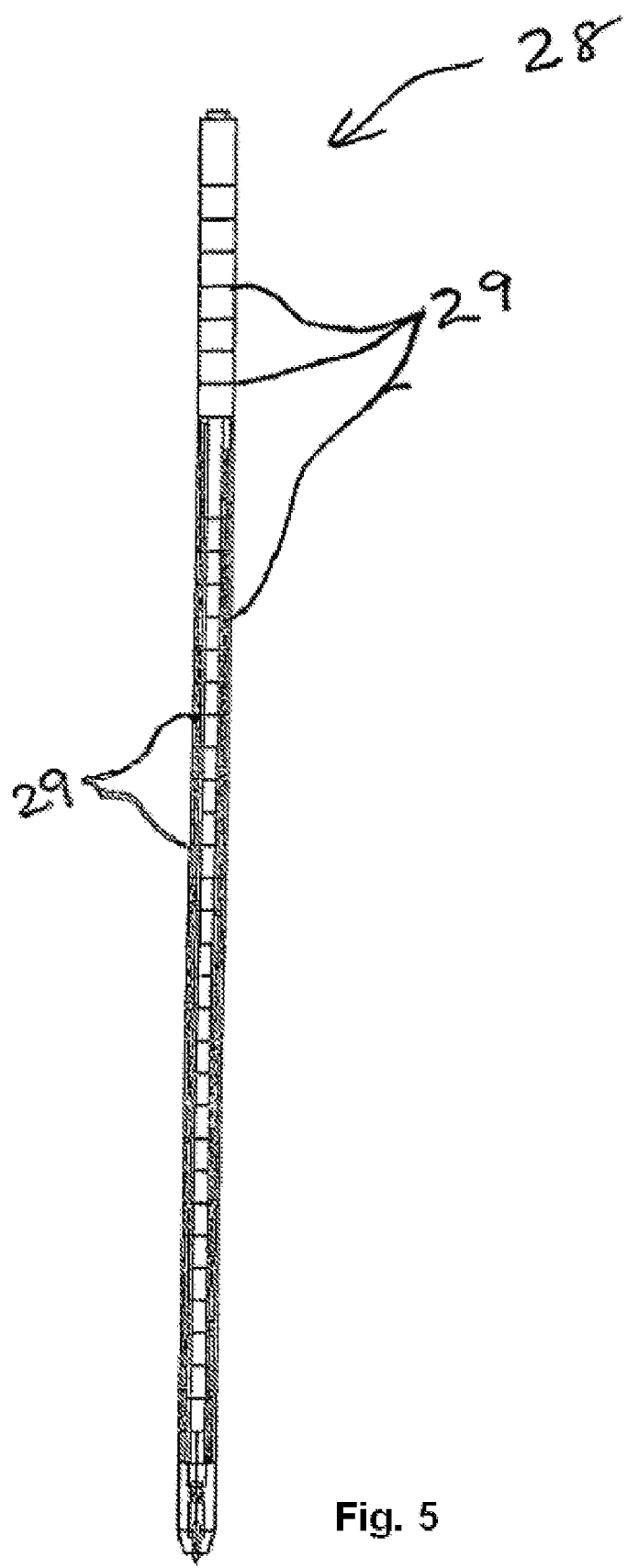
FIG. 5 is an elevation view of the electrode array components of the embodiment of FIG. 1.

Referring again to the drawings, FIG. 4 is seen to be an enlarged view of the lower portion of the processing tower 20 of FIG. 1. It can be seen that a fluid access port 40 is provided in base 42 of the processing tower. Fluid access port 40 is seen to be in communication with fluid flow channel 44. Preferably sample fluid containing the target analyte is fed upwardly through the processing chamber 26, although in alternative embodiments a downward flow can be employed. Suitable seals, for example o-ring seals are employed in accordance with standard fluid design techniques for providing a fluid tight assembly. As best seen in FIG. 4, electrode array 28 is positioned in cylindrical passageway 24, concentric with rotor 22. Similarly, rotor 22 is seen to be essentially concentrically mounted within stator 30. Rotational drive means 46 is mounted in base 42 of processing tower 20, to provide rotational drive for rotor 22 during operation of the processing tower. As best seen in FIG. 5, electrode array 28 is an elongate cylindrical assembly with ring electrodes 29 formed thereon at axially locations. Alternative suitable electrode configuration will be apparent to those skilled in the art given the benefit of this disclosure.

Figure 6:
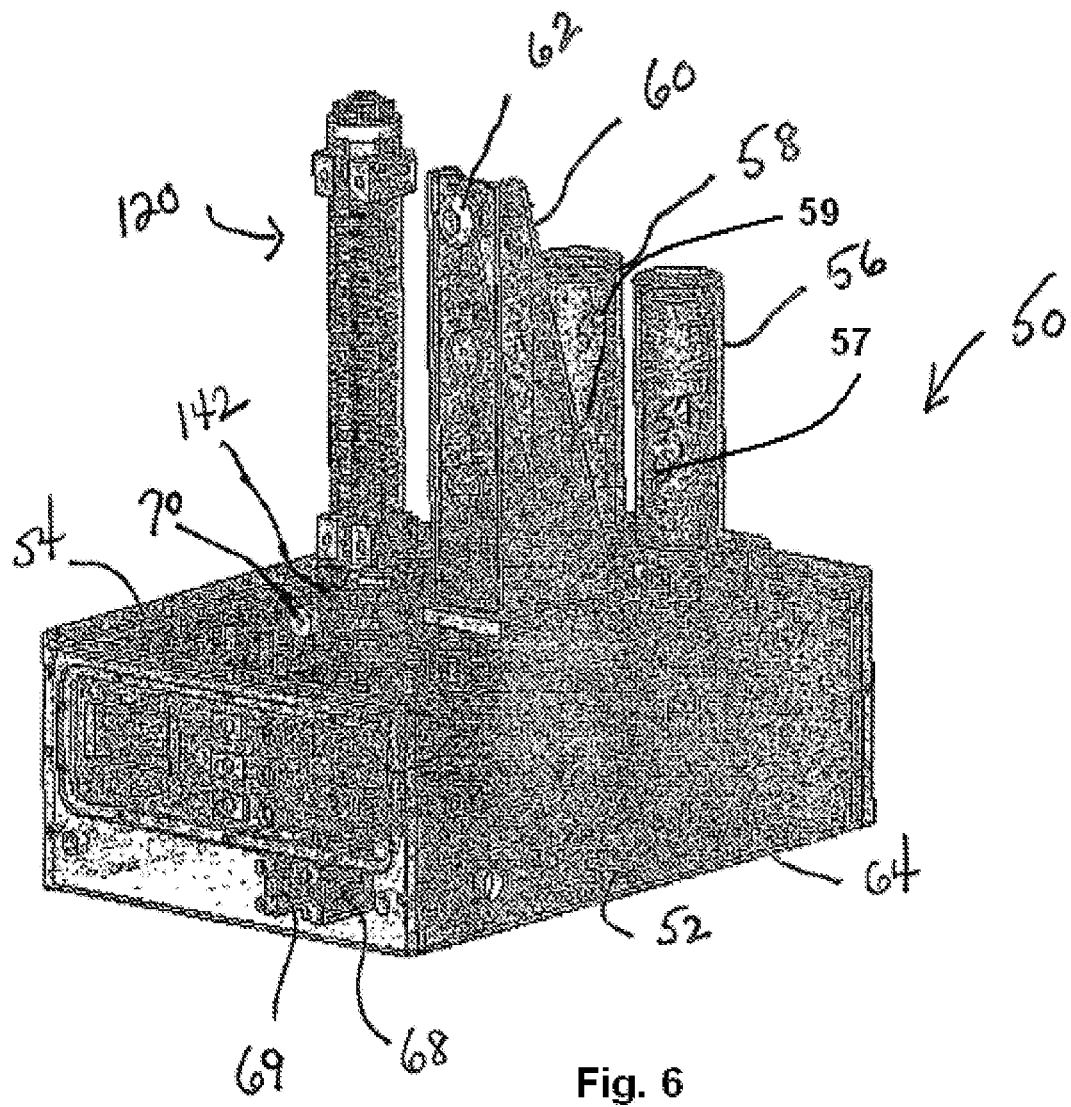
FIG. 6 is a prospective view of an electrophoretic processing system in accordance with an embodiment of the invention, comprising a separation chamber in accordance with the embodiment of FIG. 1.
Figure 7:
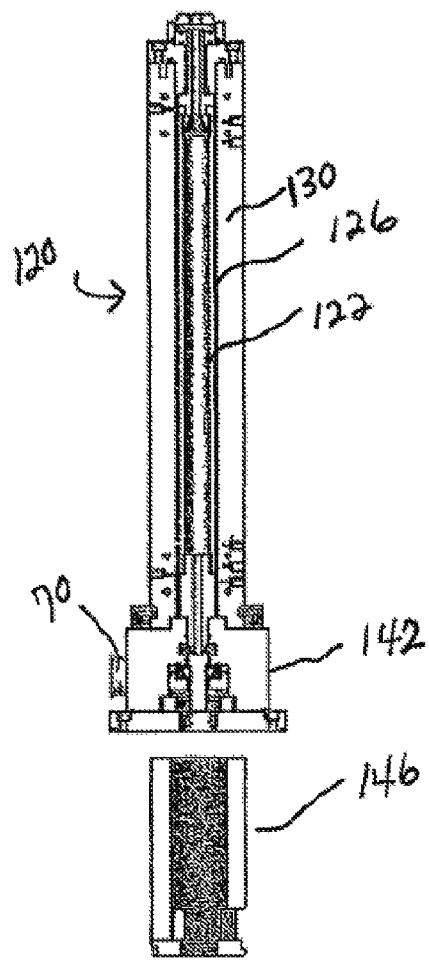
FIG. 7 is an elevation view of the separation column of the system FIG. 6.
Figure 8:
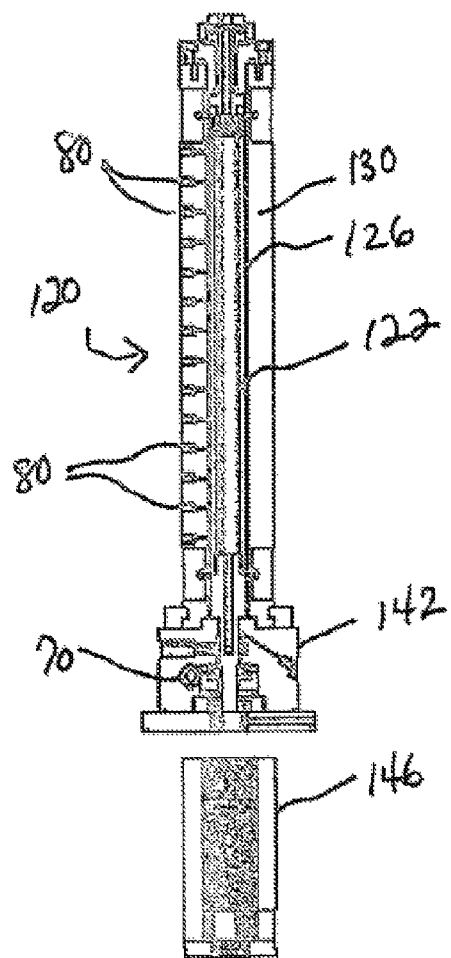
FIG. 8 is an elevation view of the separation column of the system of FIG. 6, taken from an angle perpendicular to that of FIG. 7.
Figure 9:
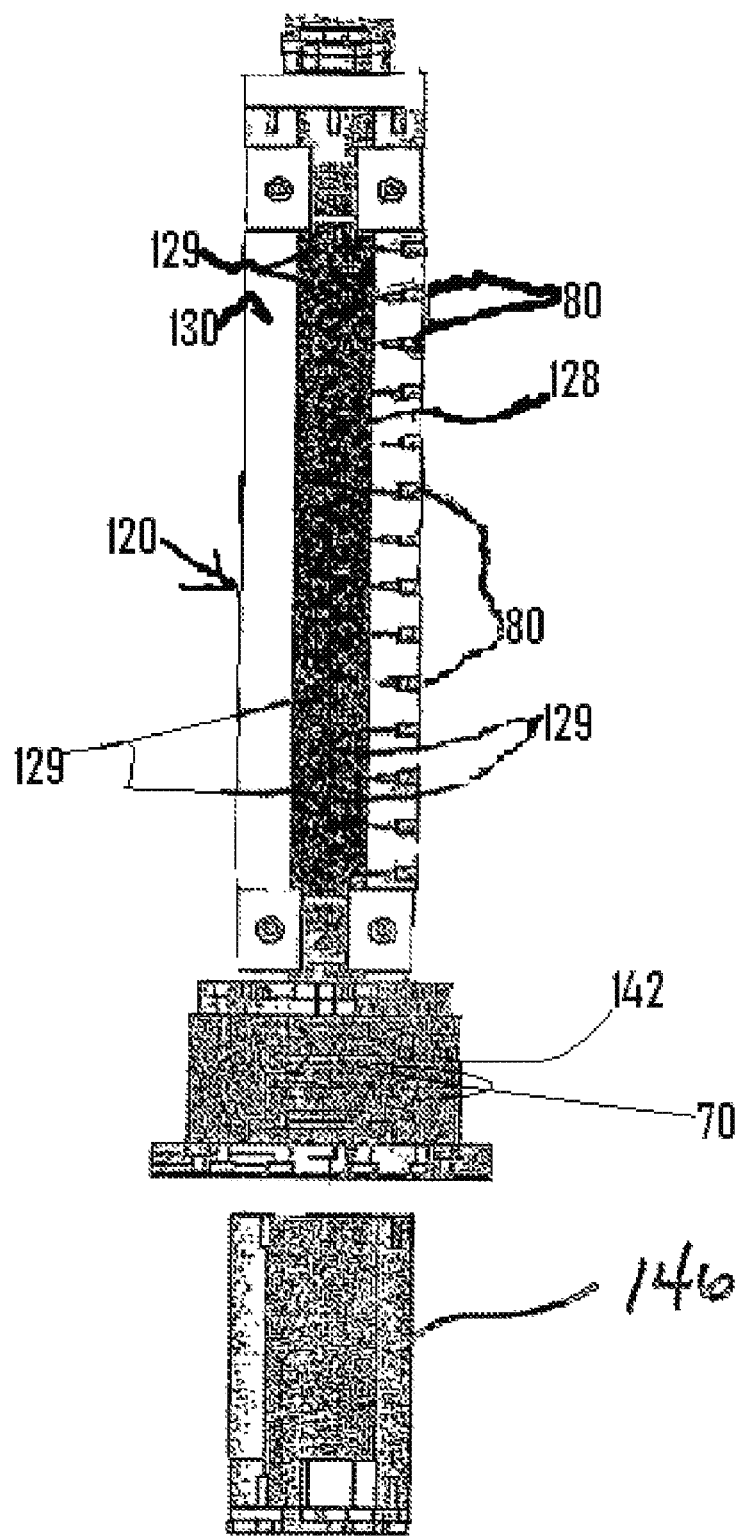
FIG. 9 is an elevation view of the separation column of the system of FIG. 6, is showing the electrode erray.
Figure 10:
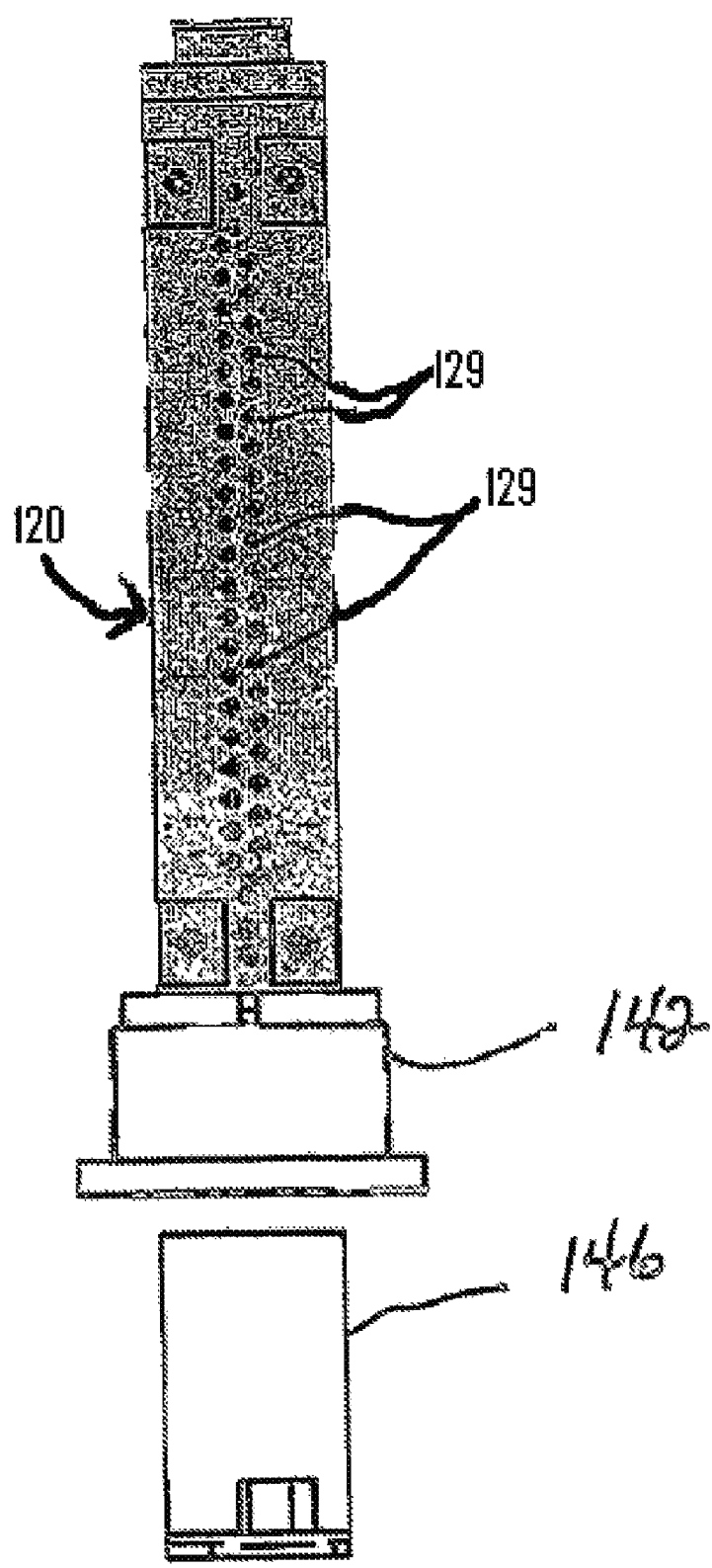
FIG. 10 is a simplified view corresponding to the view of FIG. 9.

Referring now to FIG. 6, an electrophoretic processing tower 120 similar to that of FIG. 1, is seen to be incorporated in a vertical orientation as a component of electrophoretic processing system 50. System 50 comprises a support base 52. On upper surface 54 of support base 52 is mounted processing tower 120, fluid reservoirs 56, 58 and mounting bracket 60 for mounting one or more multi-valves 62 for feeding fluid to the processing chamber through any one or more of the take-off ports (discuss further below), or for withdrawing fluid through such take-off ports. For clarity of illustration, the fluid connection tubes between the system components are not shown. It can be seen, however, that reservoir 56 has a fluid port 57 and reservoir 58 similarly has a fluid port 59. Multi-valve 62 would have fluid connection individually to multiple of the take-off ports. Visible in phantom within support base 52 are fluid pumps 64 and 66 associated with reservoirs 56 and 58, respectively. Also visible in phantom within the support base 52 are drive means supports 68 and 69 to provide support for rotational drive means 146 also housed within the support base 52. Processing tower support 142 comprises a position adjuster 70 operative to adjust the vertical position of the rotor relative to the stator. The adjuster employs a worm gear arrangement, although alternative suitable means will be apparent to those skilled in the art given the benefit of this disclosure. The position adjuster is operatively connected to at least one of the processing chamber surfaces and is operative to adjust the axial position of the processing chamber surfaces relative to each other. In this regard, it is found to be a significant advantage to precisely vertically align the annular ridges or other surface shaping of the rotor and stator to each other.

Referring now to FIGS. 7-10 various elevation views are seen of the processing tower 120 of the electrophoretic processing system 50 of FIG. 6. In FIGS. 7-10 the processing tower 120 is seen to comprise a stator 130 and rotor 122 defining between them annular processing chamber 126 having surface shaping operative to induce or aid in forming vortex stabilized flow in accordance with principles disclosed here. A series of take-off ports 80 are axially spaced along the height of the processing chamber 126. Take-off ports 80 provide fluid communication at a series of vertical heights for fluid communication controlled multi-valve 62. An electrode array 128 positioned at the center of the processing tower comprises a series of vertically spaced electrodes 129, which are operative to establish a dynamic field gradient within the processing chamber 126. Preferably, the level of energization, that is, voltage level applied to each of the electrodes (or to subsets of the electrodes) is computer controlled, either entirely automatically in accordance with sensor information, such as fiber optic sensor information (further described elsewhere herein) or by an operator using the computer as a control interface. Suitable control programs for controlling the electrodes are commercially available or can be readily developed by those skilled in the art given the benefit of this disclosure. Likewise, suitable power supplies (not shown) are commercially available.

Figure 11:
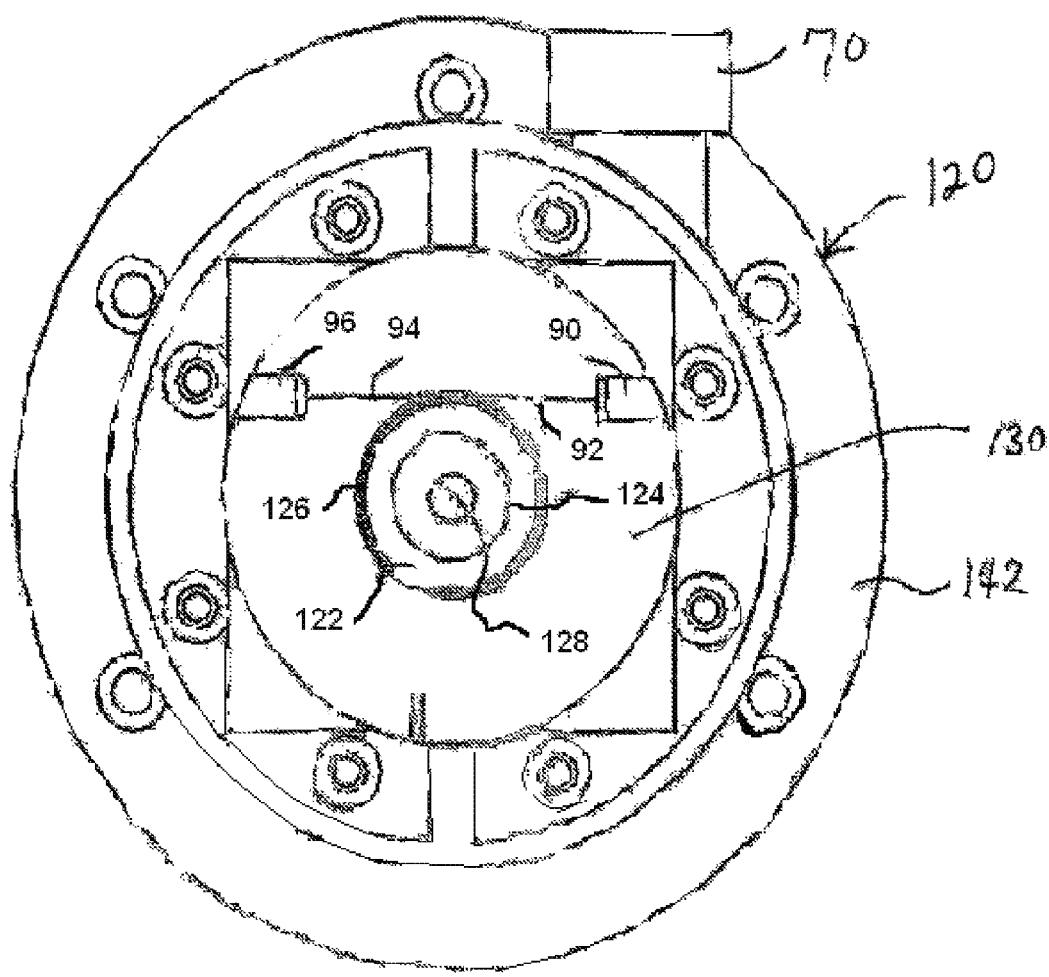
FIG. 11 is a cross section plan view of the separation column of the system of FIG. 6.

Referring now to FIG. 11, a cross-sectional view of the processing tower 120 is shown. Stator 130 and rotor in 122 are seen to be concentrically mounted, with electrode array 128 concentrically mounted at the center of buffer channel 124 within rotor 122. Also seen is an optical port 90 in optical communication with a fiber optic line 92 leading to processing chamber 126. A second fiber optic line 94 is in optical communication with a second optical port 96. The first optical port is operative to expose sample fluid within processing chamber to ultraviolet light or other suitable wavelengths. Thus, optical line 92 is seen to extend through stator 130 to an access point at the surface processing chamber 126. The second optical port 96, via fiber optic line 94 to the processing chamber 126 is operative to receive transmitted or reflected light from sample fluid within the processing chamber. More specifically, the second optical port is positioned to receive light from fluid exposed to ultraviolet light via the first port. Optical port 96 is connected by suitable optical communication line (not shown) to an optical sensor for receiving and digitizing the signal. Preferably a series of such optical ports are positioned axially along the height of the processing chamber 126.

Although the precise dimensions of a processing tower and of the other components of a processing system in accordance with this disclosure will vary in accordance with the needs of a particular application, a typical embodiment of the processing tower 120 in FIG. 6 would have an overall processing chamber height of approximately one foot, with a processing chamber radial gap dimension of approximately 2 millimeters. More generally, the typical embodiments will employ a processing chamber having a vertical dimension of 5 to 30 inches, more typically 10 to 20 inches, and a radial gap dimension of 0.5 to 5 millimeters, more typically 1 to 3 millimeters.

The surface shaping of the processing chamber surfaces will typically have a radial dimension of approximately 10% to 50% of the radial dimension of the processing chamber, more preferably 20% to 40%, e.g., about 25% to 35%. The electrodes of the central electrode array may be separated approximately 1 centimeter from each other in the axial direction, although more or less spacing may be suitable depending upon the particular intended use of the device. The buffer running over the electrode array within the rotor in the embodiments shown in the drawings is an advantageous arrangement, in that it not only provides cooling but it also washes away electrophoresis by-products. The rotor, as noted above, may be formed of ceramic. In any event, it should be electrically permeable, robust and non-conductive. It also should be highly thermally conductive and machineable for ease of manufacture. Ceramics such as boron nitride are found suitable, such as grade AX05, commercially available from St. Gobain. In accordance with the embodiments shown in the drawings, the rotor is tubular in form, having a radial wall thickness of approximately 0.5 centimeter for a processing tower having a height of 12 inches. As noted above, materials suitable for the membrane will be apparent to those field in the art given the benefit of this disclosure. Suitable materials include, for example, cellulose acetate, polyether sulfone and the like. The membrane must be operative to keep the analyte from being drawn into the ceramic pores (typically approximately 5 microns in size). Alternative embodiments include providing the membrane without the ceramic rotor and, rather using instead a scaffolding over which the membrane is mounted. The rotor structure must, of course, be sufficiently robust for its intended use at rotational speeds. Typical rotor speeds are about 50 rpm for a rotor having an outside diameter of approximately 1 inch and a height of about 12 inches. Higher and lower rotational speeds will be suitable, depending upon the particular application intended for the device, and depending also on the dimension of the particular device. It will be apparent also to those skilled in the art, given the benefit of this disclosure, that the electrode array could be mounted on the stator instead or in addition to those mounted on the rotor. In addition, in certain embodiments it is advantageous to provide electrode pairs on the outside of the processing chamber to apply a bias field. In general, regarding the steepness of the field gradient, a steeper slope will provide sharper bands or with smaller separation between bands, while a higher slope gradient will provide less narrow bands spaced further from each other. The dynamic field gradient can, in accordance with the needs of the particular intended application, be linear, exponential, non-uniform, etc. The gradient can even reverse slope over a portion of the axial length of the processing chamber. Suitable multi-valves, i.e., multi-port valves, are available, for example, from Vici.

While certain preferred embodiments of the invention has been illustrated and described, it will be appreciated that various changes can be made therein without departing from the spirit and scope of the invention.

We claim:

1. A vortex-stabilized electrophoretic processor comprising:
   an annular processing chamber at least partly defined by concentric first and second processing chamber surfaces, at least one of the processing chamber surfaces being rotatable relative to the other processing chamber surface;

an electric field generator operative to be energized to establish a dynamic field gradient within the processing chamber;

at least one fluid port in fluid communication with the processing chamber; and a position adjuster connected to at least one of the processing chamber surfaces and operative to adjust the axial position of the processing chamber surfaces relative to each other, wherein at least one of the processing chamber surfaces has shaping comprising multiple spaced annular ridges extending toward the other of the processing chamber surfaces operative to induce formation of axial counter-rotating circumferential vortices in fluid introduced into the annular processing chamber.

2. The vortex-stabilized electrophoretic processor of claim 1 further comprising a second fluid port in fluid communication with the processing chamber, the first and second fluid ports being axially spaced from each other along the processing chamber.

3. The vortex-stabilized electrophoretic processor of claim 2 further comprising a fluid take-off port in fluid communication with the processing chamber and positioned axially between the first and second fluid ports.

4. The vortex-stabilized electrophoretic processor of claim 1 wherein the first processing chamber surface has shaping comprising annular ridges spaced axially a first distance from each other and the second processing chamber surface has shaping comprising annular ridges spaced axially a second distance from each other, the first distance being twice the second distance.

5. A vortex-stabilized electrophoretic processor comprising:

an elongate annular processing chamber between concentric first and second processing chamber surfaces, at least one of the processing chamber surfaces being rotatable relative to the other processing chamber surface, an electrode array operative to be energized to establish a dynamic field gradient within the processing chamber;

at least one fluid port in fluid communication with the processing chamber; and an optical port in optical communication with the processing chamber, operative to expose fluid within the processing chamber to Ultraviolet light.

wherein at least one of the processing chamber surfaces has shaping comprising multiple spaced annular ridges extending toward the other of the processing chamber surfaces.

6. The vortex-stabilized electrophoretic processor of claim 5 wherein the processing chamber further comprises a series of take-off valves axially spaced along the processing chamber.

7. The vortex-stabilized electrophoretic processor of claim 6 further comprising a multi-valve in fluid communication with more than one of the take-off valves of the processing chamber, the multi-valve being operative to withdraw fluid selectively from any of said take-off valves with which it is in fluid communication.

8. The vortex-stabilized electrophoretic processor of claim 5 further comprising at least one reservoir operative to hold and feed fluid to the processing chamber.

9. The vortex-stabilized electrophoretic processor of claim 5 wherein the rotor comprises porous ceramic.

10. The vortex-stabilized electrophoretic processor of claim 9 wherein the rotor further comprises a membrane over the outside surface of the ceramic.

11. The vortex-stabilized electrophoretic processor of claim 5 wherein the optical port comprises a fiber optic line extending through the stator.

12. The vortex-stabilized electrophoretic processor of claim 5 further comprising a first optical port operative to expose fluid within the processing chamber to ultraviolet light, and a second optical port operative to receive ultraviolet light from fluid within the processing chamber exposed to ultraviolet light from the first optical port.

13. A method of vortex-stabilized electrophoretic processing, comprising:

introducing a fluid sample comprising an analyte into an annular processing chamber of an electrophoretic processor comprising concentric first and second processing chamber surfaces forming the processing chamber between them, at least one of the processing chamber surfaces being rotatable relative to the other processing chamber surface, an electric field generator operative to be energized to establish a dynamic field gradient within the processing chamber; and at least one fluid port in fluid communication with the processing chamber; wherein at least one of the processing chamber surfaces has shaping comprising multiple spaced annular ridges extending toward the other of the processing chamber surfaces; and a position adjuster connected to at least one of the processing chamber surfaces and operative to adjust the axial position of the processing chamber surfaces relative to each other, establishing axial counter-rotating circumferential vortices in the fluid sample in the processing chamber by rotation of the one processing chamber surface relative to the other processing chamber surface; and establishing a dynamic field gradient in the processing chamber by energizing the electric field generator.

14. The method of vortex-stabilized electrophoretic processing in accordance with claim 13 wherein the field generator comprises an electrode array and establishing a dynamic field gradient in the processing chamber by energizing the electric field generator comprises energizing electrodes of the electrode array, the electrodes being spaced axially along the processing chamber and being independently controllable as to voltage level.

15. A vortex-stabilized electrophoretic processor comprising:

an elongate annular processing chamber between the inside surface of an elongate cylindrical stator and the outside surface of an elongate cylindrical rotor positioned in the stator, the outside surface of the rotor being concentric with the inside surface of the stator, the rotor being rotatable about its longitudinal axis relative to the stator;

an electrode array positioned concentrically in the rotor, comprising a series of independently controllable electrodes spaced axially from one another within the rotor and operative to be energized to establish a dynamic field gradient in the processing chamber; and first and second fluid ports axially spaced from each other along the processing chamber.

16. The vortex-stabilized electrophoretic processor of claim 5 wherein the rotor comprises a tube of porous rigid material.

17. he vortex-stabilized electrophoretic processor of claim 16 wherein the rotor further comprises a permeable membrane on the outer surface of the porous rigid material.

18. The vortex-stabilized electrophoretic processor of claim 17 wherein the membrane is operative to not pass product.

19. The vortex-stabilized electrophoretic processor of claim 17 wherein the membrane is operative to not pass protein.

20. The vortex-stabilized electrophoretic processor of claim 17 wherein the rotor tube of porous rigid material comprises ceramic.

21. The vortex-stabilized electrophoretic processor of claim 20 wherein the ceramic has pores approximately 5 microns in size.

22. The vortex-stabilized electrophoretic processor of claim 5 wherein the rotor comprises scaffolding and a membrane mounted over the scaffolding.

23. The vortex-stabilized electrophoretic processor of claim 1 wherein the position adjuster is a worm gear arrangement.

24. The vortex-stabilized electrophoretic processor of claim 1 further comprising an optical port in optical communication with the processing chamber, operative to expose fluid within the processing chamber to Ultraviolet light.

25. The vortex-stabilized electrophoretic processor of claim 24 wherein the optical port comprises a fiber optic line extending through the stator.

26. The vortex-stabilized electrophoretic processor of claim 1 further comprising a first optical port operative to expose fluid within the processing chamber to ultraviolet light, and a second optical port operative to receive ultraviolet light from fluid within the processing chamber exposed to ultraviolet light from the first optical port.

27. The vortex-stabilized electrophoretic processor of claim 1 wherein the annular processing chamber is positioned between the inside surface of an elongate cylindrical stator and the outside surface of an elongate cylindrical rotor positioned in the stator, the outside surface of the rotor being concentric with the inside surface of the stator, the rotor being rotatable about its longitudinal axis relative to the stator.

28. The vortex-stabilized electrophoretic processor of claim 1 wherein the electric field generator is an electrode array comprising a series of independently controllable electrodes spaced axially from one from another within the rotor.

29. The vortex-stabilized electrophoretic processor of claim 1 wherein the processing chamber further comprises a series of take-off valves axially spaced along the processing chamber.

30. The vortex-stabilized electrophoretic processor of claim 29 further comprising a multi-valve in fluid communication with more than one of the take-off valves of the processing chamber, the multi-valve being operative to withdraw fluid selectively from any of said take-off valves with which it is in fluid communication.

31. The vortex-stabilized electrophoretic processor of claim 1 further comprising at least one reservoir operative to hold and feed fluid to the processing chamber.

32. The vortex-stabilized electrophoretic processor of claim 1 wherein the rotor comprises a tube of porous rigid material.

33. The vortex-stabilized electrophoretic processor of claim 32 wherein the porous rigid material comprises porous ceramic.

34. The vortex-stabilized electrophoretic processor of claim 33 wherein the ceramic has pores approximately 5 microns in size.

35. The vortex-stabilized electrophoretic processor of claim 32 wherein the rotor further comprises a membrane over the outside surface of the porous rigid material.

36. The vortex-stabilized electrophoretic processor of claim 32 wherein the membrane is operative to not pass product.

37. The vortex-stabilized electrophoretic processor of claim 32 wherein the membrane is operative to not pass protein.

38. The vortex-stabilized electrophoretic processor of claim 1 wherein the rotor comprises scaffolding and a membrane mounted over the scaffolding.

39. The vortex-stabilized electrophoretic processor of claim 5 further comprising a position adjuster connected to at least one of the processing chamber surfaces and operative to adjust the axial position of the processing chamber surfaces relative to each other.

40. The vortex-stabilized electrophoretic processor of claim 39 wherein the position adjuster is a worm gear arrangement.

41. The vortex-stabilized electrophoretic processor of claim 5 wherein the elongate annular processing chamber is positioned between the inside surface of an elongate cylindrical stator and the outside surface of an elongate cylindrical rotor positioned in the stator, the outside surface of the rotor being concentric with the inside surface of the stator, the rotor being rotatable about its longitudinal axis relative to the stator.

42. The vortex-stabilized electrophoretic processor of claim 5 wherein the electrode array comprises a series of independently controllable electrodes spaced axially from one from another within the rotor.

43. The vortex-stabilized electrophoretic processor of claim 5 wherein a first fluid port and a second fluid port are axially spaced from each other along the processing chamber.

44. The vortex-stabilized electrophoretic processor of claim 5 wherein the inside surface of the stator has shaping comprising annular ridges extending toward the rotor and spaced axially a first distance from each other, and the outside surface of the rotor has shaping comprising annular ridges extending toward the stator and spaced axially a second distance from each other, the first distance being half the second distance.

* * * * *